United States Patent [19]

Dechene et al.

[11] Patent Number: 5,015,954

[45] Date of Patent: May 14, 1991

[54] MAGNETIC RESONANCE ANALYSIS IN REAL TIME, INDUSTRIAL USAGE MODE

[75] Inventors: Ronald L. Dechene, Boxford, Mass.; Thomas B. Smith, Atkinson, N.H.; Scott A. Marino, Haverhill, Mass.

[73] Assignee: Auburn International, Inc., Danvers, Mass.

[21] Appl. No.: 374,493

[22] Filed: Jun. 30, 1989

[51] Int. Cl.$^5$ .......................................... G01R 33/20
[52] U.S. Cl. .................................................. 324/307
[58] Field of Search ................ 324/300, 307, 309, 310, 324/311, 312, 313, 314, 318, 322; 128/653

[56] References Cited

U.S. PATENT DOCUMENTS

| | | | |
|---|---|---|---|
| 4,820,983 | 4/1989 | Bendall et al. | 324/307 |
| 4,832,037 | 5/1989 | Granot | 324/307 |
| 4,853,635 | 8/1989 | Cuppen | 324/307 |

Primary Examiner—Michael J. Tokar
Attorney, Agent, or Firm—Jerry Cohen

[57] ABSTRACT

Magnestic resonance system for industrial purposes comprising sample throughput system (P, LI, V1, V2) magnetic field adjustment (120, 124) and thermal adjustment (134–138 and 142–146). The resonance is established by a coil (100), excited by a transceiver (104) and interacting with the sample and the magnetic field at resonance to establish received and digitized free induction decay curve forms (C) which are synthesized into bound (Gaussian) and unbound (exponential) components—pairing simplified high speed computation means with repetitive test sequence and thermal controls that systematically minimize errors to assure reliable determination of target nuclei quantities in successive samples from an industrial process.

11 Claims, 2 Drawing Sheets

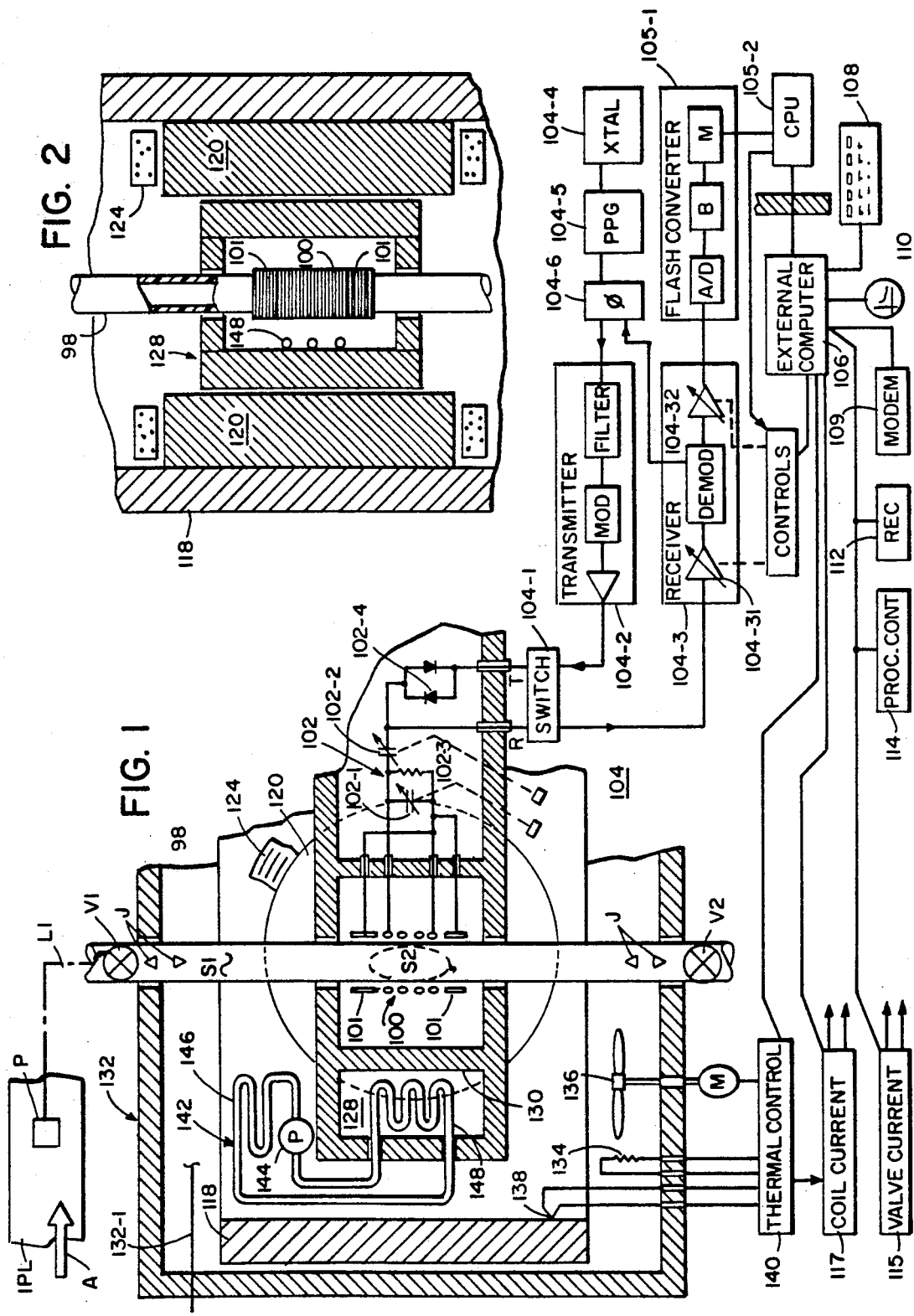

MAGNETIC RESONANCE ANALYSIS IN REAL TIME, INDUSTRIAL USAGE MODE

FIELD OF THE INVENTION

The present invention relates to an instrument for measurement of the type and quantity of lattice bound and free magnetically active nuclei within a sample through pulsed nuclear magnetic resonance (NMR) techniques.

BACKGROUND OF THE INVENTION

NMR techniques have grown extensively over the past forty years, most notably in the medical instrumentation areas where in vivo examination of various parts of the human body can be seen and in clinical research laboratory uses. In addition there has been some use and interest in the application of these techniques to industrial instrumentation and control tasks. The present invention enables effective utilization (technically and economically) of pulsed NMR techniques in industrial areas to replace or complement existing optical and radiant energy-based instrumentation.

The following is a brief review of NMR theory and concepts pertinent to understanding the present invention. The term, magnetic resonance imaging, or MRI, used below, is an alternative name for NMR. NMR signal is more easily understood by the human eye and brain. Approximately one third of the elemental isotopes and certain compounds with non-zero spin quantum numbers are magnetically active and suitable for MRI detection.

In a simplified model, a spinning isolated nucleus will align itself either with or against a static magnetic field. There will be a nearly equal number of nuclei aligned in each direction since there is only a small energy difference between these two states so a thermal equilibrium exists between these two states. However, statistically there will be a small number of excess nuclei in the lower energy state. It is these excess nuclei which give rise to MRI signals. The term "nuclei" will subsequently refer only to magnetically active nuclei.

Nuclei in a magnetic field will precess similar to a spinning top, because there is an angular acceleration produced by the interaction of the magnetic field and the magnetic moment of the nuclei. This precession occurs in the direction of the magnetic field. Quantum mechanics shows that only a selected number of possible alignments is possible. The precessional frequency is determined by which alignment occurs and the magnetic properties of the nucleus being studied. The fundamental MRI signal is derived from inducing transitions between these different alignments. This is often done by using the magnetic component of an applied RF (radio frequency) signal. When this component is applied perpendicularly to the magnetic field a resonance occurs at a particular RF frequency where transitions between the different alignments happen. This resonance typically occurs in the Megahertz frequency ranges when a strong magnetic field is used. This field is in the 1 Tesla (10,000 Gauss) order of magnitude (i.e. 0.1-2 T).

The effect of a nucleus bonded in a lattice to other nuclei has a great effect on the resonance frequencies. The effect of the other components and the bonding create secondary effects and shielding which cause the resonance frequencies to be different. In effect the chemical environment affects the resonance frequencies and the signal strength.

Pulsed MRI spectroscopy is one specific technique to which the present invention is drawn. This technique uses a radio frequency burst or pulse which is designed to excite all the nuclei of a particular nuclear species. After the application of the pulse there occurs a free induction decay (FID) curve associated with the excited nuclei. Traditional Fourier Transform analysis generates a frequency spectrum which can be used to advantage in studying the nuclei of interest. The duration of the pulses, the time between the pulses, the pulse phase angle and the use of chemical reactants in the sample are parameters which affect the sensitivity of this technique. These frequency techniques are not easily useable in industrial applications, especially on-line applications.

An object of this invention is an improved measurement system which leads to accurate, fast determination of the types and quantity of the nuclear species of interest.

A further object of the invention is to utilize time domain analysis in achieving such system.

Another object of this invention is its application to the industrial, on-line problems of measuring the controlling processes.

The principal variable of interest is moisture, with distinction between free and bound water in an organic or inorganic substance based on hydrogen nuclei precession analysis. But other parameters can be measured based on hydrogen or other sensitive species including e.g., sodium. It is an object of this invention to accommodate a variety of such measuring tasks.

Another object is to accommodate the dynamics of industrial on-line applications including variations of density, temperature, packing and size factors, friction and static electricity, vibration and frequent, repetitive, cyclic and non-cyclic measurements.

Another object of the invention is to use magnetic resonance techniques in polymer analysis, including density and/or melt index measurement.

Another object is to enhance accuracy and reliability of data obtained.

It is an object of the invention to achieve the necessary practical economies consistent with the foregoing objects.

SUMMARY OF THE INVENTION

The present invention provides a materials measurement system using magnetic resonance hardware, controls (and related data capture and data reduction means and steps) and techniques, preferably in the time domain. The system is utilizable in connection with capture of data from a continuous production line or like repetitive measurement system.

The magnetic resonance imaging ("MRI") hardware and controls of the measuring system of the invention comprise economically scaled down and industrially hardened portions, relative to the widely used laboratory systems. A magnetic essentially fixed field comprises closely spaced pole pieces with a 4,000-8,000 Gauss field (about 4,700 Gauss, nominally). Helmholtz coils are provided which are adjustable to provide rapid adjustments for the precise, correct field and overlaid with coarse, slower adjustments to thermal environment. This is to assure that the product of a materials related constant (gamma) times magnetic field, which is resonant frequency, will match excitation frequency.

Still further fine adjustment is made in signal processing as described below.

Radio frequency energy is transmitted to a sample from a transceiver to modify the protons' precession in the sample volume portion in the fixed magnetic field. The energy transmission is quickly terminated after a short pulse duration (applied in consecutive sub-cycles as alternate transmit pulses which are 180 degrees out-of-phase in consecutive transmissions for baseline error elimination as hereinafter described) and the sample volume relaxes and transmits a return pulse of decaying energy, i.e., the free induction decay (FID) curve. The system is operated in a resonant condition, i.e.—the return pulse being an essentially infinite wavelength of a beat frequency product of demodulated excitation and return signals. A range of hundreds of thousands of points FID curves and of component curves are matched to closest fitting functions in the time domain (in contrast to prior art linear approximation of components related from one or a few—less than a dozen points of FID curve). This approach is used since the time decay is very fast and there have been insufficient techniques used to capture the subtleties of the curves. The curves are used to determine the quantity of a particular nuclear species in the sample and the relative proportions of that species which are bound by a lattice structure and that which is unbound. These distinctions are determinable by reconstructed time-zero intercepts of FID curve portions.

The return pulse decay curve is analyzed, according to the present invention into a correct decay curve portion in low computational power, inexpensive data systems rather than in state of the art, high computational power systems. These decay curve portions, once determined properly, can be extrapolated back to a zero-time origin (or other substitute for such origin related to it) to give correct nuclear data and secondary information based on nuclei data, e.g., moisture content of the sample, density, relative composition of multiple species in the sample, melt index, etc.

It has been discovered that a further limitation of temperature is significant. We have discovered that in some materials, e.g., wheat, the Gaussian curve portion of a free induction decay curve is significantly shifted at different temperatures and this in turn shifts the derived zero intercept. Recognizing this problem, a solution is imposed by taking integrals of square function derivatives of areas under the composite free induction decay curve and under a component curve of the latter generated by bound nuclei (nominally a Gaussian curve). The bound curve is derived from the subtraction of another exponential (and in fact exponential to a high degree of approximation). The ratio of the square root of those areas provides a more reliable ratio than the intercept derived ratios in cases of temperature shift of samples.

It must be noted that in an industrial situation temperature control of a sample per se is prohibited because it would invalidate the sample's reliability. Yet there is no time for stabilization, calibration and other artifacts of adjustment for temperature. The present invention meets this problem by the various levels of thermal response described above.

The invention accommodates great streams of data in practical ways through features, described below, which are interrelated to the thermal controls to provide a measuring system meeting the foregoing objects. The materials of construction are also integrated into the reliability considerations, as described below. Measurement of a sample is accomplished in less than thirty seconds (often under ten seconds, in contrast to hours-long measurements of many prior art systems.

The measurements made through the present invention based on ratios of intercepts and/or integrated areas under curves are independent of weight or volume of sample in a measuring region whereas precise weight measurement is a necessary feature—and limitation of—many prior art systems.

The system of the invention can also be used in prior art formats.

Other objects, features, and advantages will be apparent from the following detailed description of preferred embodiments taken in conjunction with the accompanying drawing(s) in which:

BRIEF DESCRIPTION OF THE DRAWING(S)

FIGS. 1 and 2 are lateral and cross-sections of a preferred embodiment of the invention including electrical block diagram components.

DETAILED DESCRIPTION OF PREFERRED EMBODIMENTS)

Figure 3:
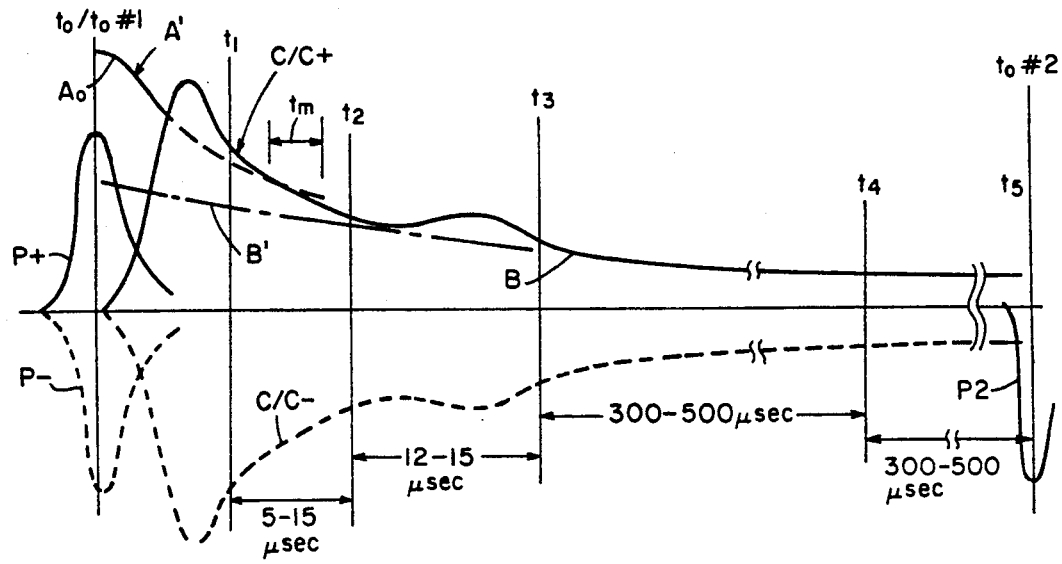
FIG. 3 shows the voltage-time waveforms of free induction decay (FID) of the embodiment of FIGS. 1-2 in the course of operation.

FIGS. 1-2 show transverse and cross sections with block diagram inserts of a first embodiment of the invention. An industrial process line IPL has material flowing as indicated by arrow A. Some of the material is captured by a probe P and fed through an inlet line LI to a sample region S1. The said region is defined by a tube 98 typically a foot long made of an essentially non-magnetic, nonconducting material which does not itself generate substantially interfering FID signals (glass, certain ceramics, certain plastics or hybrids). The sample region is defined between inlet and outlet valves V1 and V2. Gas jets J are also provided. These are pulsed on/off repeatedly to agitate fluent sample materials during sample admission and expulsion. The region S2 is the critical portion of the sample. It is surrounded by a sample coil 100 tuned to resonance and driven by a tuning circuit 102 and related transmitter/receiver controller 104. Grounded loops 101 are active Lenz Law shields which are provided above and below coil 100 to help shape the field of coil 100—i.e., contain the field established by an excitation pulse. The controller 104 includes an on-board microprocessor and required power supply elements, memory, program and I/O decoding suitable to interconnect to the hardware shown and to an external microcomputer 106 with keyboard 108, monitor (or other display) 110, recorder 112 and/or process controller 114 (to control the process at IPL). The operator initiates and controls operation from the display keyboard 108 and the resulting data and signals are subsequently shown on the display 100 and utilized in 110, 112 and/or 114. The computer 106 also controls instrument operation conditions.

The region S2 of the tube 98 and coil 100 are in a static but adjustable crossing magnetic field defined by a magnetic assembly 116 which comprises a yoke 118, pole pieces 120, surrounding Helmholtz coils 124, and a coil current generator 122. The critical sample region S2 of the type 98 and magnet are contained in a metallic (but non-ferromagnetic) box 126 with highly thermally conductive face-plates 128 and internal partitions 130 and over-all mass related to each other to minimize harmonics and other interferences with a microwave signal emitted from coil 100 to a sample and/or returned from the sample for pick-up by coil 100 and its tuned circuit 102 and transmit/receive controller 104.

The magnetic assembly 116 including yoke 118, and other parts therein as shown on FIGS. 1-2, is in turn contained in an environmental control chamber 132 with gas fill and purge controls (not shown), an internal gas heater 134, a motor M driving fan 136, and a temperature sensor 138 which can be applied to the yoke or other detection region whose temperature is reflective of the temperature at pole pieces 120 and in the sample region therebetween. A thermal controller 140 processes temperature signals from 138 to adjust heating-/circulation at 134/136 as a coarse control and to adjust current through the Helmholtz coils 124 at magnet pole pieces 120 as a sensitive and fast fine control, as well as implementing general control instructions of computer 106. Further thermal stabilization is provided by a closed loop heat exchanger 142 having pump 144 and coils 146 attached to yoke 118 and coils 148 attached to the plates 128 of box 126.

The strength, consistency and constancy of the magnetic field between poles 120 in the region S2 of the sample is thus controlled by a uniform base magnetic field in the entire region S2. The Helmholtz coils 124 are energized by the coil current controller 140 to accurately trim the final magnitude of the field in which the sample is placed. This field is the vector addition of the fields due to the magnet poles 120 and the Helmholtz coils 124. The controller 140 sets the current through the Helmholtz coils 124 using current generators. The coils 124 are wound around the magnet 110 such that the magnetic field created by the current in the coils 114 can add to or subtract from the field created by the magnet pole pieces 120. The magnitude of the current through the coils 124 determines the strength of the field added to or subtracted from the field due to the magnet pole pieces 120 (and related yoke structure) alone.

The actual determination of the current through the Helmholtz coils is accomplished by carrying out the magnetic energy and resonance techniques hereinafter described in preliminary runs and adjusting Helmholtz current until the maximum sensitive ressonance is achieved.

The major elements of electrical controls are in tuner 102, including coils 100 and 101 and variable capacitors 102-1 and 102-2, resistor 102-3 and diodes 102-4 and constructed for tuning to Q of twenty to fifty to achieve coil 100 resonance, and control 104 including a transmit/receive switch 104-1 a transmitter 104-2 and receiver 104-3, a crystal oscillator 104-4, gated pulse generator (PPG) 104-5, and phase shifter 104-6. The crystal provides a nominal twenty Megahertz carrier which is phase modulated or demodulated by the MOD, DEMOD elements of transmitter 104-2 and receiver 104-3. The receiver includes variable gain amplifier elements 104-31 and 104-32 for operation. The analog signals received are fed to a high speed flash converter 105-1 and internal (to the instrument) CPU element 105-2, which provides data to an external computer 106 which has a keyboard 108, monitor 109, modem 110, recording elements 112 and process controller elements 114, e.g., for control of valves V1, V2 via valve controls 115 and/or to coil current controls 122, all via digital-analog converters (not shown).

The excitation of coil 100 and excitation-precession of the sample's proton content and subsequent relaxation/decay produces a received FM signal that, after demodulation, controlled gain amplification, A/D conversion and plotting of points has the free induction decay (FID) curve shape C shown in FIG. 3. FIG. 3, voltage-time trace, shows the elements of a "cycle" (with (+) and (−) sub-cycles) of excitation of a sample and free induction decay. In each (+)/(−) sub-cycle a pulse of excitation energy is applied. The excitation pulse center is taken as t0. The transceiver 104 electronic components do not receive effectively until saturation effects are overcome at t1. Then a useable curve C(+) or (C−) is developed. The signal processing equipment can add or subtract consecutive C+ and C− forms for useful adjustment as described below.

The FID curve data is stored in the external computer 106 where a program finds the best curve to fit each stored FID curve. The FID curve C has two component parts shown as A and B in FIG. 3. The curve A which dominates the first part of the FID curve is a Gaussian curve while the B curve which dominates that later part of the FID curve is an exponential decay. The Gaussian and exponential portions are respectively controlled by bound and unbound proton content of the samples (e.g., (1) water or hydration molecules and other water (moisture) content of the sample mass, (2) crystalline and amorphous contents where they both occur, including mixtures of highly and lightly polymerized materials and (3) components a mixed elastomer-polymer). The determination of the type of curve which makes up the FID curve C is important because once the curves are known they can be extended back to a time origin (shown as t0-1), i.e., excitation of a Cycle 1), which is at the theoretical center of the transmitted burst signal. This is important since there are saturation effects of the instrument's electronic gear which occur from the end of the burst signal to t1. During this time measurements cannot be accurately taken, yet the area of interest under the curve, which is a measure of the number of nuclei in the sample, extends from t0 to t4 beyond which the curve is too small to matter and the electronics need recovery time to prepare for the next cycle (beginning with a pulse centered at t0-2).

Each (sub) cycle goes on to t5 to allow for recovery i.e., essentially full relaxation of the protons of the sample—before beginning a new transmit signal burst (t0-2). Typically, an excitation pulse interval is five to ten microseconds, the t0—t1 time is five to fifteen microseconds (the shorter the better), t1-t2, where effects due to bound nuclei (Gaussian) are predominant is five to fifteen microseconds duration (with critical measurement taken at a narrower region tm); t2-t3 is an unclear transition region of fifteen to twenty-five microseconds duration, t3-t4 is a region where the unbound (exponential) component predominates and it is three hundred to five hundred microseconds duration during that part of the decay. The closest exponential curve is fitted to the C curve in the t3-t4 region where the C and B curves are essentially equal and this B curve is extrapolated back to t0, i.e., establishing a curve B and its phantom B′ component and B0 intercept at t0. This exponential curve is subtracted from the C curve in the area (t2-t4) where the A (Gaussian) curve is dominant. The resulting curve is then fitted with the best least squares Gaussian curve. This best Gaussian curve is then extrapolated back to t0 to establish A including its phantom A' component and A0 intercept at t0.

The resulting data utilized in the computer 106 (FIGS. 1-2) is the A curve and the B curve and ultimately their intercepts at t0 and the B0/A0+B0 ratio thereof. Each of these curves (and their intercepts) has been experimentally and theoretically related to the same nuclei of interest, but with the group of the nuclei which yield the A curve (Gaussian) bound in a lattice structure. The nuclei which yield the B curve (exponential) are unbound.

The data can be used as a QC type measurement or as an on-line control parameter which is fed back to control a process, back in line IPL (FIG. 1) or related equipment (e.g., in drying or baking a food product, conducting a continuous chemical or metallurgical re-action process, etc.)

The form of the input operating parameters of the system can be wide reaching to include previously stored parameters in PROMs or ROMs or inputs sent in over telephone line and modem 110. The generation of the RF signal can be accomplished with many techniques including a coil or antenna arrangement. The steady magnetic field can be generated by electromagnets, permanent magnets, electromagnetics with superconducting winding or other standard techniques of generating magnetic fields.

Figure 4:
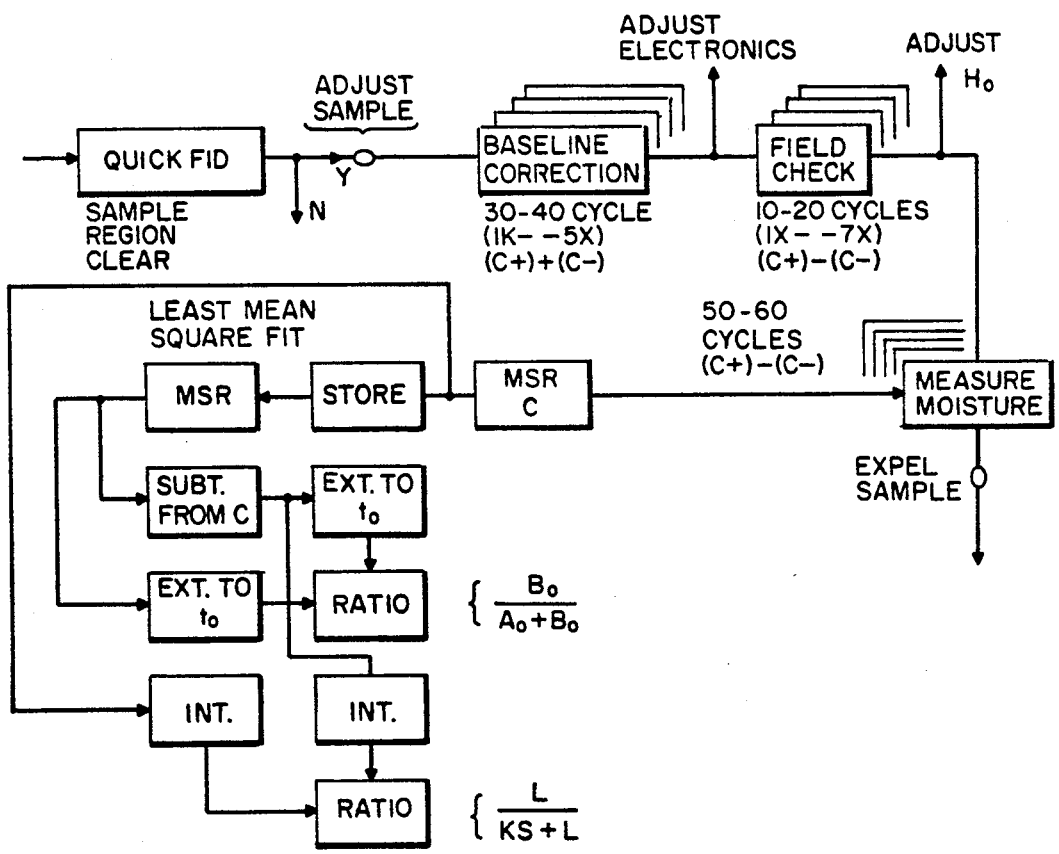
FIG. 4 is a flow chart of measuring steps utilizing the FIGS. 1-2 apparatus including its signal processing elements, (the activity of which is illustrated by the FIG. 3 waveforms).

FIG. 4 is an expanded flow chart showing the steps of measurement to establish effective industrial measurement. First a single free induction decay curve C is established to see if the sample area is clear (Quick FID) in an abbreviated cycle of attempting to establish a curve C. If the sample region is not clear (N), measurement is interrupted to allow valve V2 (re)opening and operation of jets J and gravity to clear the region. A new Quick FID step establishes clearance. Then a sample is admitted by closing value V2, opening valve V1 and making such adjustments of probe P and line LI as may be necessary (if any) to assure sample acquisition. Jets J adjust and stabilize the new sample.

Temperature controls 134-138 and 142-146, described above, establish very coarse and less coarse thermal controls countering sample temperature variations.

An electronic signal processing apparatus baseline is established in 30-40 cycles (each having (+) and (−) sub-cycles with addition of (C+) and (C−) to detect an offset and compensate for it). Further adjustment is established by coils 24 to adjust HO and this is enabled by ten to twenty field check cycles of FID curve generation. The (C−) FID is subtracted from the (C+) FID, i.e., the absolute C values are added to obtain a workable FID derivative—which has a maximum value at resonance. HO is adjusted via coil current generator 122 and coils 124 until such maximum is achieved. These measurements are taken in a reliable region for such purpose, i.e., the expontial region t3-t4 [the above baseline measurements are also taken there]. Adequate field adjustment is usually made in less than seven cycles.

Then fifth to five hundred cycles are conducted to obtain a useable measurement. Each of those fifty to five hundred cycles involves a modulated FM transmission/reception/flash A-D conversion, and storage of data. The curves are then averaged for curve fitting, t0 intercept and B0/A0+B0 ratio establishment. Similar cycles, but somewhat abbreviated can be applied for Quick FID, field check and baseline correction purposes. Each of the sub-cycles [(+) and (−)] of each such cycle involves a capture of thousands of FID points and utilization of hundreds of such points in data reduction.

Where multiple cycles are applied for a single measurement, the amplitudes of (digitized) curve C points are stored and a least squares fit to such data points is established. Further, plus and minus values are taken in alternation to eliminate zeroing errors as noted above.

The area under a squaring derivation of the FID curve is integrated ("int.") and the area under a squared derivative of the desired exponential is integrated and a ratio is established, the square root of which is $L/(KS+L)$ where L is liquid (moisture) value derived from the exponential, K a constant and S is a solid (or bound proton) related quantity related to the Gaussian, $KS+L$ being total protons affected by resonance imaging (and capable of being so affected).

It has also been discovered as greater accuracy and reliability is obtained that sample tube composition can distort readings. If glass is not used (and it is preferred to avoid glass in industrial usage), then the replacement should not be a hydrocarbon plastic. But flurocarbons can be effective in several applications since signals from fluorine act out of resonance (with conditions tuned to resonance for hydrogen in moisture measurements) and can be distinguished from moisture related readings at the levels of sensitivity required for such readings and if desired can be filtered (or distinguished. In other cases of higher sensitivity measurements, e.g., for gauging relative proportions of amorphous and crystalline species in mixtures thereof, the sample container should be glass or non-protonic ceramic. In all such cases the point is to avoid sample containers with species that can couple with transmitted energy and generate a FID decay curve misreading the samples. This invention includes a system response to discovery of certain such cases not heretofore recognized.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. Nuclear magnetic resonance system for industrial process monitoring comprising:
   (a) means for accessing successive samples from an industrial process, placing them in a sample measuring region and discarding successive such samples from said sample measuring region,
   (b) means for applying a base magnetic field to the sample measuring region to effect precession of sample nuclei therein and for applying a resonant excitationpulse to the sample measuring region to modify the precession
      means defining receive antenna coil means and signal translating means interacting with a sample in said region and relaxation detected at the coil means as free induction decay signal which is measurable as a free induction decay curve via said signal translating means,
   (c) means for digitizing the free induction decay curve and automatically analyzing the digitized curve to zero-axis intercepts of and components of the decay curve, summing and extracting a ratio of the intercept of one of said components to the sum of the intercepts of said components,
and wherein:
said means (a)-(c) are constructed and arranged;
  (1) to stabilize base field application, excitation and signal translation conditions in response to variations of one or more parameters of actual condition of a sample in the sample measuring region;
  (2) to effect such extraction of ratio and related stabilization on a repeating, high speed basis for successive samples from the industrial process; and
  (3) translating at least a thousand data points in each decay curve and effecting reduction as to at least a hundred points thereof whereby sample component proportions are reliably and repeatedly measurable from sample to sample in rapid succession for on-line real time monitoring.

2. System in accordance with claim 1 wherein said base magnetic field application coil means comprise Helmholtz coil means with coarse thermal stabilization of an outer sample processing region and an intermediate stabilization of an interior sample containing region which is adjacent to pole faces of the coil and wherein the said construction arrangement for stabilization comprises coarse thermal environment coil means for the sample region, and means for fine adjustment via electromagnetic field variation to maintain resonance in the sample region.

3. System in accordance with claim 2 comprising means for effecting a further countermeasure to thermally-induced drift by adjustment of extracted decay signal.

4. System in accordance with claim 3 wherein the said means for adjustment of extracted decay signals comprise means for affecting said analysis of the free induction decay curve by areal integration of at least a discrete-function component thereof.

5. System in accordance with claim 1 wherein said means for effecting said analysis effect an extension of bound and unbound components of the decay curve to a reconstructed time-zero intercept coinciding with or related to the time of excitation leading to the decay.

6. System in accordance with claim 1 comprising a sample container essentially free of sample decay inducing ingredients in relationship to the sensitivity of measurement to be made.

7. System in accordance with claim 6 wherein the sample container is a fluorocarbon tube.

8. System in accordance with claim 6 wherein the sample container is a ceramic tube.

9. System in accordance with claim 6 wherein the sample container is a glass tube.

10. System in accordance with claim 1 constructed and arranged for measurement of moisture content.

11. System in accordance with claim 1 constructed and arranged to detect proportions of amorphous and crystalline components of mixtures thereof.

* * * * *